US00PP20736P2

(12) United States Plant Patent
Kapiteijn

(10) Patent No.: US PP20,736 P2
(45) Date of Patent: Feb. 9, 2010

(54) *ZANTEDESCHIA* PLANT NAMED 'CAPTAIN AMIGO'

(50) Latin Name: ***Zantedeschia* sp.**
Varietal Denomination: Captain Amigo

(75) Inventor: Anthonius Simon-Johannes Kapiteijn, Anna Paulowna (NL)

(73) Assignee: Kapitetyn Breeding BV, Anna Paulowna (NL)

( * ) Notice: Subject to any disclaimer, the term of this patent is extended or adjusted under 35 U.S.C. 154(b) by 413 days.

(21) Appl. No.: 11/809,247

(22) Filed: May 31, 2007

(51) Int. Cl.
*A01H 5/00* (2006.01)

(52) U.S. Cl. ..... Plt./490

(58) Field of Classification Search ..... Plt./490
See application file for complete search history.

*Primary Examiner*—Kent L Bell
(74) *Attorney, Agent, or Firm*—Mark P. Bourgeois

(57) ABSTRACT

A new cultivar of *Zantedeschia* plant named 'Captain Amigo' that is characterized by green leaves with white spots and yellow orange colored inflorescences.

1 Drawing Sheet

Botanical classification: *Zantedeschia* sp.
Variety denomination: 'Captain Amigo'.

BACKGROUND OF THE INVENTION

The present invention relates to a new and distinct cultivar of *Zantedeschia* plant botanically known as *Zantedeschia* sp. and hereinafter referred to by the cultivar name 'Captain Amigo'.

'Captain Amigo' is a hybrid that originated from the induced hybridization in 1998 of the female or seed parent a proprietary *Zantedeschia* sp. identified as number 45 (not patented) and the male or pollen parent a proprietary *Zantedeschia* sp. identified as number 05 (not patented). The cultivar 'Captain Amigo' was selected by the inventor in 2001 as a single plant within the progeny of the stated cross in Breezand, The Netherlands.

Asexual reproduction by tissue culture of the new cultivar 'Captain Amigo' was first performed in 2001 in De Goorn, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Zantedeschia* cultivar 'Captain Amigo'.

1. *Zantedeschia* 'Captain Amigo' exhibits green leaves with white spots.
2. *Zantedeschia* 'Captain Amigo' exhibits yellow orange colored inflorescences.

The closest comparison cultivar is *Zantedeschia* 'Neroli'. The new cultivar 'Captain Amigo' is distinguishable from 'Neroli' by the following characteristics:

1. 'Captain Amigo' has smaller inflorescences than 'Neroli'.
2. 'Captain Amigo' has yellower inflorescences than 'Neroli'.

The new cultivar 'Captain Amigo' is distinguishable from the male parent *Zantedeschia* identified as number 05 in having a stronger stem and bigger inflorescences. The new cultivar 'Captain Amigo' is distinguishable from the female parent *Zantedeschia* identified as number 45 in having a larger number of inflorescences.

BRIEF DESCRIPTION OF THE DRAWING

The accompanying photograph illustrates the distinguishing traits of *Zantedeschia* 'Captain Amigo'.

The plant in the photograph shows an overall view of a 24 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Zantedeschia* cultivar named 'Captain Amigo'. Data was collected in Boskoop, The Netherlands from 24 month old greenhouse grown plants in 17 cm. containers. The time of year was Spring and the average temperature was 24 degrees Centigrade during the day and 17 degrees Centigrade at night. No photoperiodic treatments were used. Gibberallic Acid was used to induce flowering. Color determinations are in accordance with The Royal Horticultural Society Colour Chart 2001 edition, except where general color terms of ordinary dictionary significance are used. The growing requirements are similar to the species. 'Captain Amigo' has not been tested under all possible conditions and phenotypic differences may be observed with variations in environmental, climatic, and cultural conditions, however, without any variance in genotype.

Botanical classification: *Zantedeschia* sp. 'Captain Amigo'.

Use: Ornamental.

Parentage: 'Captain Amigo' is a hybrid plant that resulted from the induced hybridization of the following parent plants:

*Female parent.*—*Zantedeschia* sp. number 45.

*Male parent.*—*Zantedeschia* sp number 05.

Vigor: Moderate.

Growth rate: Moderate.

Growth habit: Sparcely branching from base, upright.
Plant shape: Inverted triangle.
Suitable container size: 14 cm diameter container.
Height: Average 44.3 cm to top of leaf plane, 46.4 cm to top of inflorescences.
Width: Average 59.2 cm. in width.
Hardiness: USDA Zone 10.
Propagation: Tissue Culture.
Time to initiate roots: Approximately 540 days to produce roots on an initial cutting at between 12–25° Centigrade.
Crop time: 720 days.
Root system: Fine and fibrous.
Stem: No stems, Leaves grow directly from base, Average 3 clumps.
Foliage:
*Texture*.—Smooth on both sides, slightly leathery.
*Leaf arrangement*.—Alternate.
*Compound or single*.—Single.
*Leaf shape*.—Narrow cordate.
*Leaf apex*.—Pungent.
*Leaf base*.—Cordate.
*Leaf length*.—Average 21.3 cm in length.
*Leaf width*.—12.7 cm in width.
*Quantity of leaves per clump*.—Average 4.
*Pubescence*.—Absent.
*Leaf margin*.—Entire, wavy; lower half of each leaf more wavy than upper half.
*Vein pattern*.—Pinnate.
*Young leaf color* (*upper surface*).—In between 137A and 146A with a few small dots colored 157C.
*Young leaf color* (*lower surface*).—137B with a few small dots colored 157C.
*Mature leaf color* (*upper surface*).—137A dotted N155A. Dots have average dimensions of 7 mm in length and 1.5 mm in width.
*Mature leaf color* (*lower surface*).—137B dotted N155A. Dots have average dimensions of 7 mm in length and 1.5 mm in width.
*Vein color* (*lower surface*).—144A.
*Vein color* (*upper surface*).—143A.
*Leaf attachment*.—Petiolate.
*Petiole length*.—Average 26.6 cm in length.
*Petiole diameter, distal*.—Average 8 mm in width, 7 mm in height.
*Petiole diameter, proximal*.—Average 1.2 cm in width, 1.2 cm in height.
*Petiole aspect*.—Rounded with an undeep rib lengthways.
*Petiole texture*.—Smooth.
*Petiole surface*.—Slightly glossy.
*Petiole color*.—144A with a base colored 145A.
*Petiole sheath dimensions*.—Average 13.9 cm in length and 6 mm in diameter.
*Petiole sheath color*.—144A with a base colored 145C.
*Durability of foliage to stress*.—Moderate to high.
Inflorescence:
*Inflorescence arrangement*.—Spathes with spadices held beyond and slightly above the foliage.
*Flowering habit*.—Continuous.
*Quantity of spathes per plant*.—6.
*Natural flowering season*.—Autumn to early spring.
*Time to flower or response time*.—8 months.
*Fragrance*.—Absent.
*Self-cleaning or persistent*.—Persistent.
*Flower longevity*.—Lasts approximately 2 months on plant.
*Spathe aspect*.—Strongly cupped with wavy margin.
*Spathe dimensions*.—Average 9.1 cm in length, 7.7 cm in width. Secondary spathe in double, inflorescences slightly smaller and shorter; 9.0 cm in length and 6.3 cm in width.
*Spathe texture*.—Glabrous, slightly leathery.
*Spathe shape*.—Broad ovate; also has a strongly cupped and trumpet-shaped appearance.
*Spathe margin*.—Entire, wavy.
*Spathe apex*.—Mucronate.
*Spathe color when opening* (*front side*).—5C, margin 53C; base 4C.
*Spathe color when opening* (*back side*).—7C, upper half near margin 42B to 42C; base 144B, midrib 143A.
*Spathe color when fully opened* (*front side*).—3A, margin 53B; base 4C.
*Spathe color when fully opened* (*back side*).—In between 1A and 151B, upper half of margin 42C; base 144A, midrib 143A.
*Spathe color fading to*.—151B to 151C with a touch of 144A.
*Spadix shape*.—Cylindrical.
*Spadix tip*.—Obtuse.
*Spadix base*.—Obtuse.
*Spadix dimensions*.—Average 3.5 cm in length and 1.1 mm in diameter.
*Spadix color when opening*.—Lower part 182B, upper part 11A.
*Spadix color when fully opened*.—Lower part 182B, upper part 11A.
*Quantity of flowers per spadix*.—Average pistilate flowers 45, staminate flowers 350.
*Spadix flower shape*.—Pistilate flowers rounded in a cross-section, staminate flowers irregular, narrow oblong.
*Spadix flower dimensions*.—Pistilate flowers 2 mm in diameter and 1 mm in depth, staminate flowers 2.0 mm in diameter and less than 0.5 mm in depth.
Reproductive organs:
*Anther color*.—14A.
*Amount of pollen*.—Low.
*Pollen color*.—8C to 8D.
*Stigma color*.—13A to 13B.
*Ovary color*.—150D.
Peduncle:
*Peduncle dimensions*.—Average 34.7 cm in length and 8.0 mm. in diameter.
*Peduncle angle*.—10°.
*Peduncle color*.—144B to 144C, lighter at the base 145D.
*Peduncle strength*.—Moderate.
Seed: Seed production has not been observed.
Disease and insect resistance: Plants of the new *Zantedeschia* have not been observed for disease or insect resistance.

The invention claimed is:

1. A new and distinct variety of *Zantedeschia* plant named 'Captain Amigo' as described and illustrated.

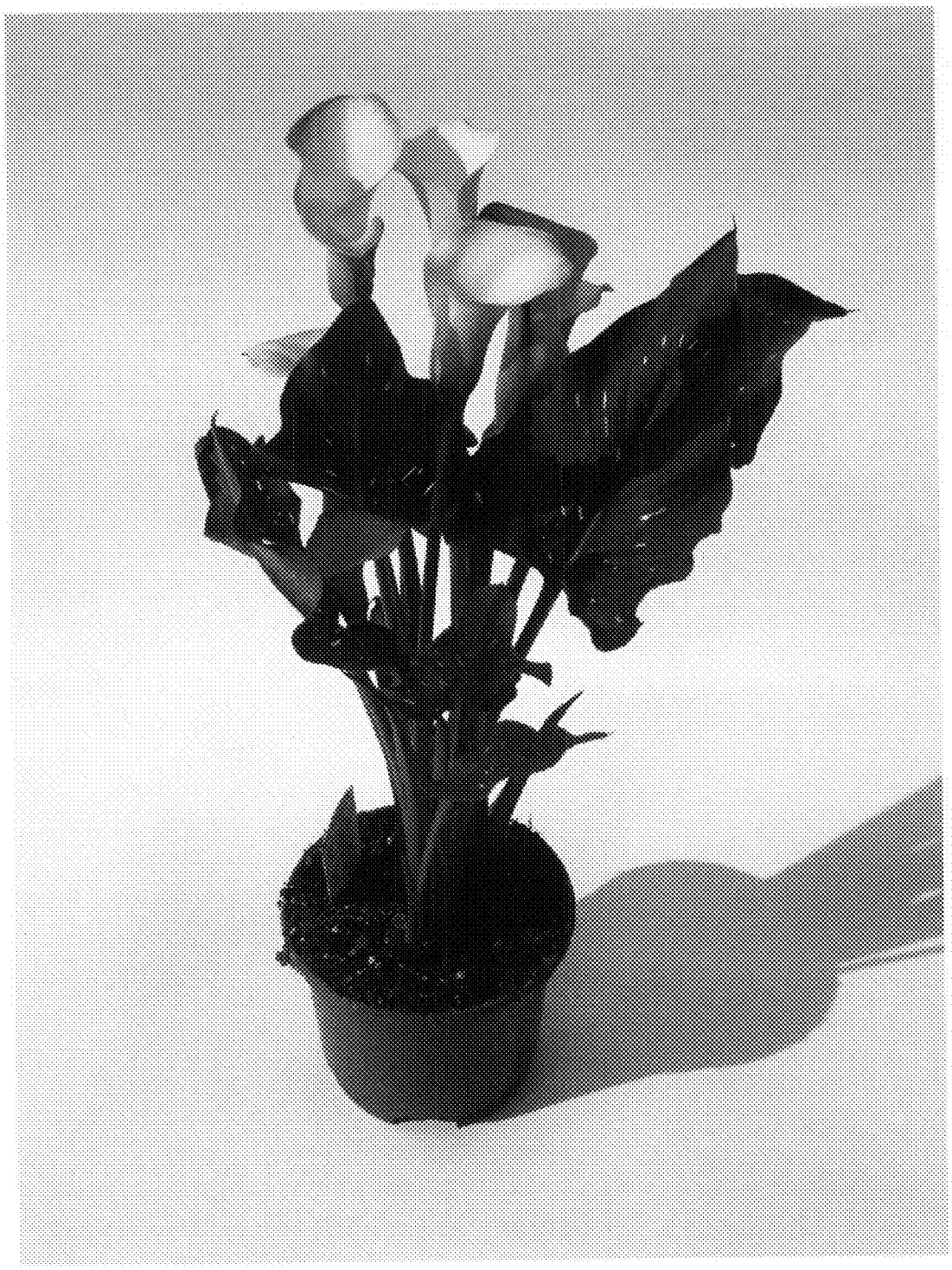

* * * * *